US006875168B2

(12) United States Patent
Bateman et al.

(10) Patent No.: US 6,875,168 B2
(45) Date of Patent: Apr. 5, 2005

(54) OOCYTE AND EMBRYO HANDLING APPARATUS

(75) Inventors: Timothy Bateman, Kent (GB); John Edward Nash, Kent (GB)

(73) Assignee: Smiths Group PLC, London (GB)

( * ) Notice: Subject to any disclaimer, the term of this patent is extended or adjusted under 35 U.S.C. 154(b) by 0 days.

(21) Appl. No.: 10/643,923

(22) Filed: Aug. 20, 2003

(65) Prior Publication Data

US 2004/0092791 A1 May 13, 2004

(30) Foreign Application Priority Data

Aug. 30, 2002 (GB) .............................................. 0220146
Jun. 11, 2003 (GB) .............................................. 0313392

(51) Int. Cl.⁷ .............................................. A61B 17/43
(52) U.S. Cl. ...................................................... 600/34
(58) Field of Search ............................... 600/633–635; 604/6.13, 43, 113, 540, 114, 523, 171; 606/20–23

(56) References Cited

U.S. PATENT DOCUMENTS

| | | | | |
|---|---|---|---|---|
| 3,971,383 A | * | 7/1976 | van Gerven | .................. 606/23 |
| 4,399,319 A | * | 8/1983 | Zinn | ............................. 174/47 |
| 4,817,624 A | | 4/1989 | Newbower | |
| 5,063,994 A | | 11/1991 | Verkaart | |
| 5,160,319 A | | 11/1992 | Emery et al. | |
| 5,360,389 A | * | 11/1994 | Chenette | ....................... 600/34 |
| 5,437,673 A | | 8/1995 | Baust et al. | |
| 6,726,654 B2 | * | 4/2004 | Rosenman | ................... 604/113 |
| 6,746,440 B2 | * | 6/2004 | Magnusson et al. | ......... 604/500 |
| 2004/0024392 A1 | * | 2/2004 | Lewis et al. | ................... 606/22 |

FOREIGN PATENT DOCUMENTS

| | | |
|---|---|---|
| EP | 0 463 837 | 1/1992 |
| EP | 1 190 684 | 3/2002 |
| WO | 00/53108 | 9/2000 |

* cited by examiner

Primary Examiner—Samuel G. Gilbert
(74) Attorney, Agent, or Firm—Louis Woo

(57) ABSTRACT

Oocyte extraction apparatus or embryo replacement apparatus has a flexible tube along which the oocyte or embryo passes. The tube extends along an outer jacket which maintains the temperature within the tube. The jacket may be thermally insulating or it may be heated such as with warmed liquid.

11 Claims, 3 Drawing Sheets

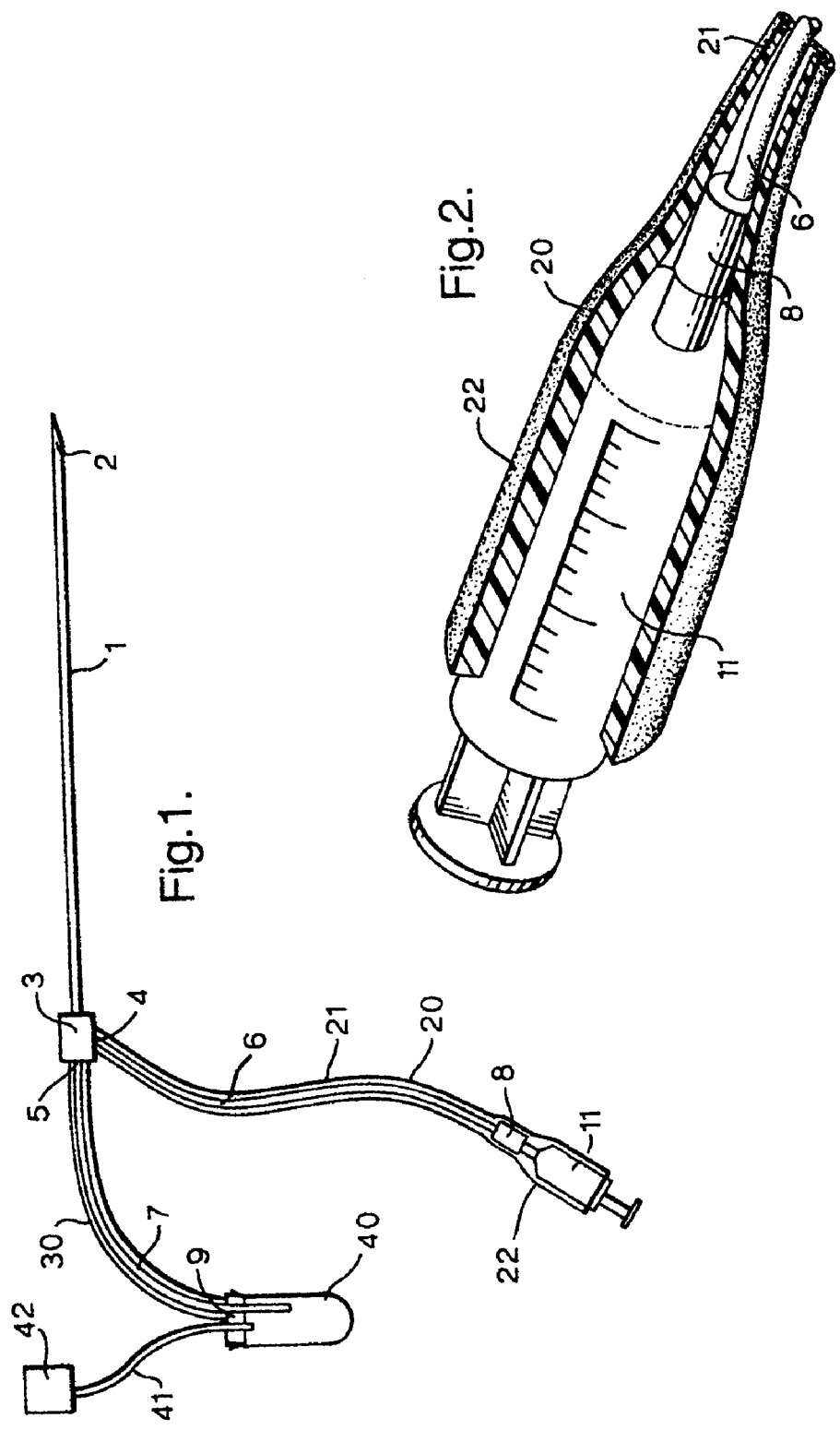

Figure 4:
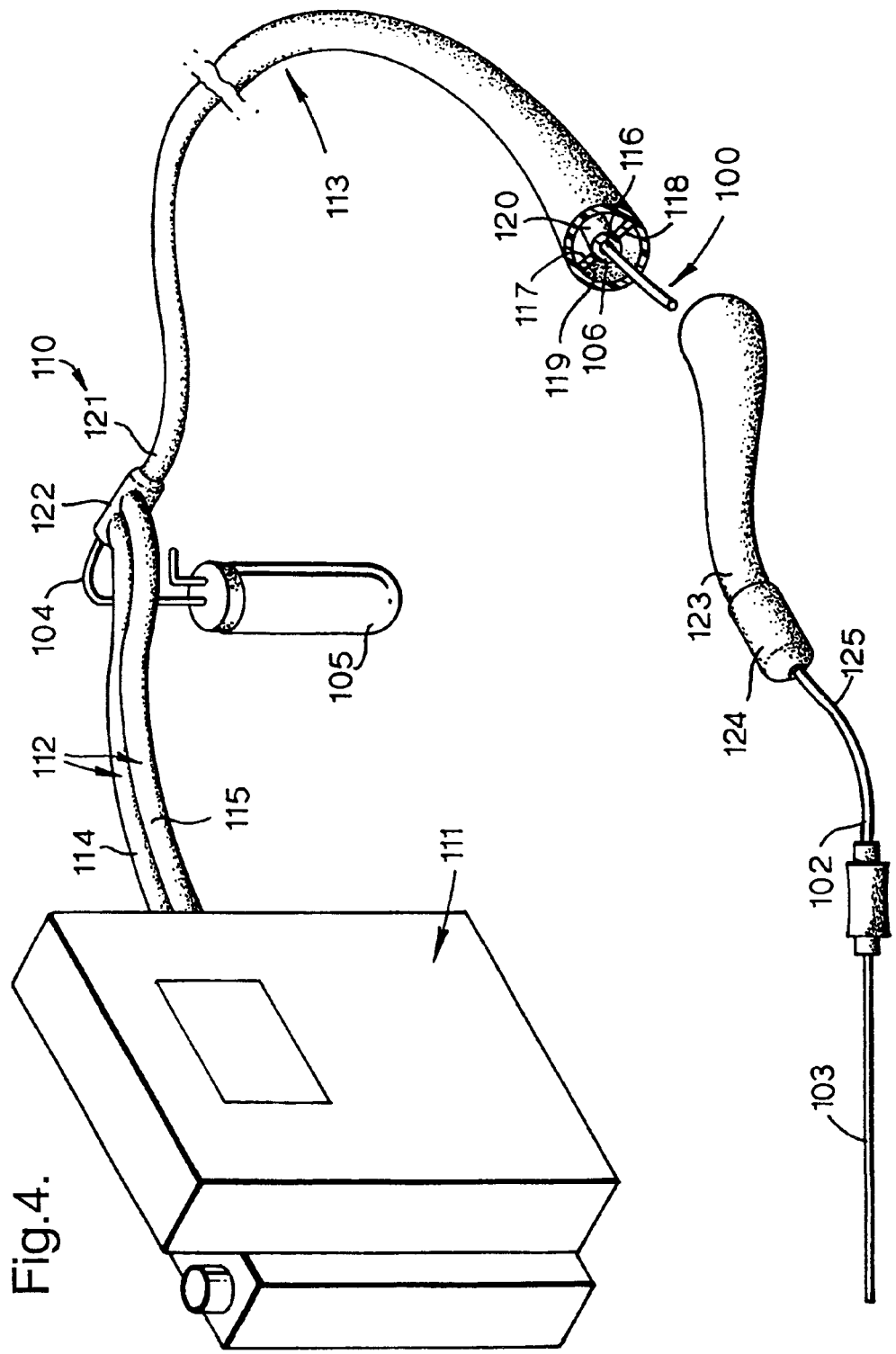

Fig.3.
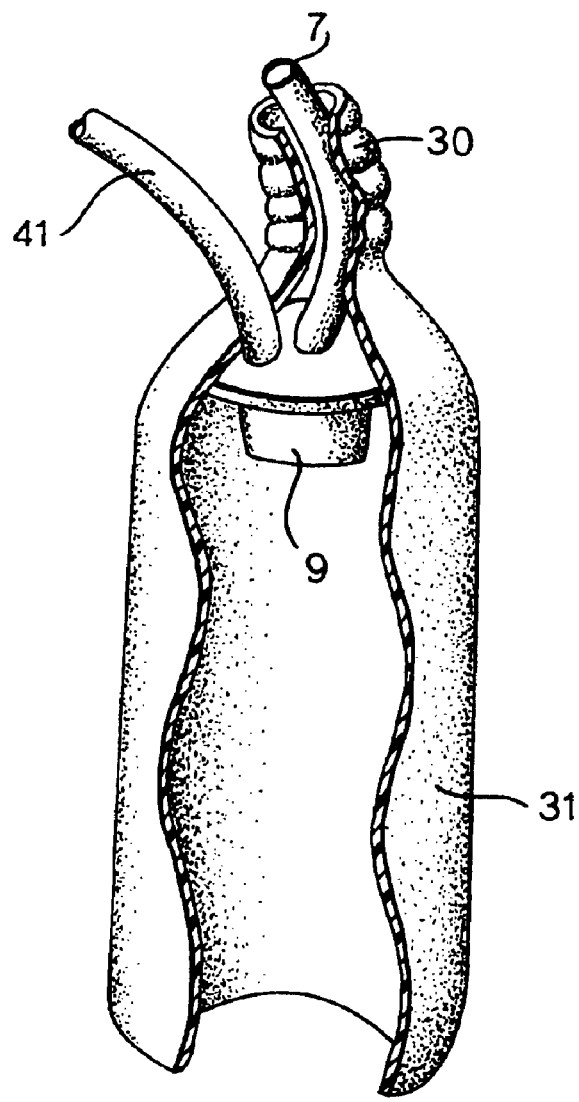
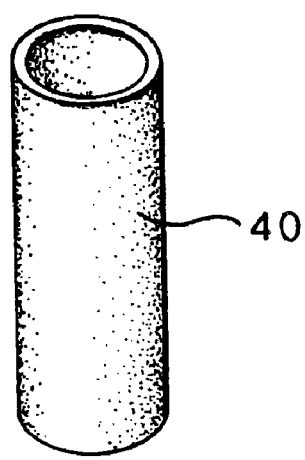

though it will normally be preferable to use separately-provided jackets so the apparatus can be sterilised and supplied ready for use.

In a further alternative arrangement shown in FIG. 4, the jacket 20 has a central bore 50 loosely receiving the flushing tube 6 and two outer channels 51 of C-shape surrounding the central bore and adapted to receive warmed fluid via an inlet 52 and an outlet 53 at the rear end of the jacket 20. The jacket 20 may be extruded from a plastics material, the ends of the outer channels 51 being blocked with a suitable filler or by other means. The jacket 30 around the aspiration tube 7 is of similar construction, with a central bore receiving the aspiration tube and two outer channels (not shown) for flow of a warmed fluid.

The tubes could be used for the handling of embryos as an alternative to oocytes.

What I claim is:

1. Apparatus for use in handling an oocyte or embryo, comprising: a tube adapted for use in the handling of the oocyte or embryo, the tube having an external surface; and an elongate jacket extending along the tube, the jacket being separate from the tube and of a thermally-insulating material with a bore along its length that receives the tube so that an inner surface of the bore of the jacket contacts the external surface of the tube and thermally insulates the tube to maintain the temperature within the tube.

2. Apparatus according to claim 1, wherein the jacket is flexible.

3. Apparatus according to claim 1, wherein the jacket is of a foamed plastics material.

4. Apparatus according to claim 1, wherein the jacket is heated.

5. Apparatus according to claim 4, wherein the jacket is heated by a warmed fluid.

6. Apparatus according to claim 5, wherein the jacket includes a central bore in which the tube is received and two outer channels along which the warmed fluid is supplied.

7. Apparatus according to claim 6, wherein the outer channels are of C shape.

8. Apparatus according to claim 6, wherein the jacket has an inlet and outlet for flow of the fluid into and out of the jacket, and wherein the inlet and outlet are located at the same end of the jacket.

9. Apparatus according to claim 1, wherein the jacket is extruded.

10. Apparatus according to claim 1, wherein the tube is adapted for flow of flushing liquid along it.

11. Apparatus according to claim 10, including a syringe connected with the tube and containing a flushing liquid for supply to the tube, and wherein the jacket extends along a part at least of the length of the syringe.

12. Apparatus according to claim 1, wherein the tube is adapted for passage of an oocyte or embryo.

13. Apparatus according to claim 12, including collecting means connected with the tube for collecting the oocyte, and wherein the jacket extends along a part at least of the length of the collecting means.

14. Apparatus for use in handling an oocyte, comprising: a dual-lumen oocyte recovery needle having a flushing lumen and a second lumen; a flushing tube connected to the flushing lumen of the needle; an aspiration tube connected with the second lumen of the needle; a first elongate jacket extending along the flushing tube, the first jacket being of a thermally-insulating material and arranged to maintain the temperature within the flushing tube; and a second elongate jacket extending along the aspiration tube, the second jacket being of a thermally-insulating material and arranged to maintain the temperature of an oocyte flowing along the aspiration tube.

15. A method of oocyte recovery comprising the steps of: connecting a tube to an oocyte recovery needle; providing a separate, elongate, thermally-insulating jacket with a bore extending along the length of the jacket; inserting the tube into the bore of the jacket such that an inner surface of the bore contacts an external surface of the tube and provides a warmed length of tube; applying suction to the tube to draw an oocyte into the tube; and collecting the oocyte after passage through the warmed length of the tube.

16. A method of oocyte recovery comprising the steps of: connecting an aspiration tube and a flushing tube to an oocyte recovery needle; maintaining the warmth of the tubes along a part at least of their length by means of respective thermally-insulating jackets each having a bore receiving a respective one of the tubes such that an inner surface of the bore contacts an external surface of the tube; applying flushing fluid via the flushing tube to the needle; applying suction to the aspiration tube to draw an oocyte into the aspiration tube; and collecting the oocyte after passage through the aspiration tube.

* * * * *

The jackets described above maintain the temperature of the syringe and tubes by being thermally insulating. They could, however, maintain the temperature in other ways. For example, the jackets could contain a volume of a previously heated substance such as a wax or gel that maintains the desired temperature by changing from a liquid to a solid at around body temperature. Alternatively, the jackets could include an electrical heating element, which could be powered by an internal battery or a remote power source.

FIG. 4 illustrates apparatus having a jacket heated by warmed fluid circulated through the jacket.

The apparatus shown in FIG. 4 has a conventional oocyte recovery tube or catheter 100 connected at its forward end 102 to a conventional oocyte recovery needle 103. At its rear end 104, the tube 100 is connected to a collection test tube 105 to which suction is applied so that the recovered oocytes are collected in the tube, in the usual way.

The apparatus has warming arrangement 110 comprising an electrically-heated fluid warmer 111, such as of the kind sold under the trade mark HOTLINE (a Registered Trade Mark of Level 1, Inc) by Level 1, Inc of Rockland, Mass., USA. The fluid warmer 111 provides a recirculating flow of water warmed to about 39° C. The warmer 111 is connected by a dual-bore tubing 112 to a heat exchanger 113. The tubing 112 has two bores 114 and 115, one for the warmed water flowing away from the warmer 111 and the other for the returned water flowing back to the warmer for reheating.

The heat exchanger 113 is preferably a modified version of that used with the HOTLINE warmer for warming infusion fluid supplied to a patient. The heat exchanger 113 is described in detail in U.S. Pat. No. 5,063,994 and in U.S. Pat. No. 5,097,898. The heat exchanger 113 is extruded from a plastics material to form a flexible, elongate, tubular jacket of circular external section. The exchanger 113 has three bores extending in parallel along the length of the exchanger. A central bore 116 is provided by a tubular portion 106 of circular section supported by two radially-extending webs 117 and 118. The webs 117 and 118 bisect an outer concentric passage around the central bore 116 into two outer channels 119 and 120 each having a C shape section. The central bore 116 opens axially at the rear end 121 of the exchanger 113 through as an end cap 122. The outer channels 119 and 120 communicate via the cap 122 with respective ones of the bores 114 and 115 of the tubing 112 and hence communicate with the fluid warmer 111. The forward end 123 of the exchanger 113 similarly has an end cap 124 within which the two outer channels 119 and 120 communicate with one another so that water supplied forwardly along one channel can flow back rearwardly along the other channel. The central bore 116 opens axially through the forward end cap 124.

The oocyte recovery tube 100 extends through the central bore 116 of the heat exchanger 113 as a close sliding fit to ensure that there is a good thermal contact between the tube and the tubular portion 106, thereby promoting efficient heat transfer to the tube. The bore 116 or tube 100 may be coated with a lubricant such as a gel to ease insertion of the tube in the bore and to improve thermal contact. The heat exchanger 113 extends along most of the length of the recovery tube 100 apart from a short section 125 at its forward end, which is exposed to facilitate manipulation, although the flexible nature of the heat exchanger does allow the remainder of the tube to be easily manoeuvred.

In an alternative arrangement, the recovery tube would not project from the heat exchanger and, instead, the hub of the needle would be combined with the end cap of the heat exchanger. Such an arrangement has the advantage of enabling the entire length of the oocyte recovery tubing to be warmed. In order to ensure that the needle could still be manipulated freely it would be preferable for the material of the heat exchanger to be selected for maximum flexibility.

In use, the fluid warmer 111 supplies warmed water at about body temperature to the rear end 121 of the exchanger 113, which flows forwardly along one channel 119 and then rearwardly along the other channel 120. This ensures that the oocyte recovery tube 100 is maintained very close to body temperature so as to maintain the recovered oocytes close to their ideal temperature during recovery.

Although alternative forms of heat exchanger could be used, the arrangement described, where fluid is supplied to and returned from the exchanger at its rear end, has several advantages. First, it keeps the forward end of the exchanger free of any additional tubing so that the surgical site is kept uncluttered and so that there is less impediment to manipulation of the forward end of the tube and exchanger. Second, the drop in temperature of the heated water flowing forwardly along the length of the exchanger is in the opposite sense to that of the water flowing rearwardly. This has the effect of reducing the overall temperature gradient along the length of the exchanger, which minimizes the thermal shock to which the oocytes are exposed.

The oocyte recovery tube could be inserted in the heat exchanger by the user and removed after use so that the heat exchanger can be reused. There is no risk of contamination because there is no direct contact with the heat exchanger itself.

The invention is not confined to oocyte recovery apparatus but could also be used in apparatus for use in handling embryos.

What is claimed is:

1. Oocyte recovery apparatus comprising a source of warming fluid, an oocyte recovery needle and a flexible tubular assembly connected at its rear end with said source and at its forward end with said needle, said tubular assembly including: a tubular passage along which an oocyte flows rearwardly of the assembly; an outer jacket surrounding said tubular passage along which warming fluid flows from said source to the forward end of the assembly to warm said tubular passage; a return path by which said warming fluid flows from the forward end of the assembly to the source; a reservoir for receiving said cocyte; and an outlet of said tubular passage to said reservoir, said outlet being located between the ends of the assembly such that said oocyte is warmed by fluid in said jacket during its passage from said needle to said reservoir.

2. Apparatus according to claim 1, wherein said outer jacket includes C-shaped channels.

3. A method of oocyte recovery comprising the steps of: connecting a tube to an oocyte recovery needle; warming said tube along a part at least of its length; applying suction to said tube to draw an oocyte into said tube; and collecting the oocyte after passage through the warmed length of said tube.

4. A method of oocyte recovery comprising the steps of: connecting an aspiration tube and a flushing tube to an oocyte recovery needle; maintaining warmth of said tubes along a part at least of their length; applying flushing fluid via said flushing tube to said needle; applying suction to said aspiration tube to draw an oocyte into said aspiration tube; and collecting the oocyte after passage through said aspiration tube.

5. Apparatus for use in extracting an oocyte comprising: a dual-lumen oocyte recovery needle having a flushing lumen and an aspiration lumen; a reservoir for receiving the oocyte; a connection between the reservoir and the aspiration lumen; a source of suction; a connection between the source of suction and the reservoir so that suction can be applied to draw an oocyte into the reservoir; a flushing tube connected with said flushing lumen; an aspiration tube connected with said aspiration lumen; a first insulating jacket extending along said flushing tube to maintain the temperature of flushing liquid in said flushing tube; and a second insulating jacket extending along said aspiration tube to maintain the temperature of an oocyte flowing along said aspiration tube.

6. Apparatus according to claim 5 including a syringe containing flushing liquid connected with said flushing tube, and wherein said first insulating jacket extends along a part at least of the length of said syringe.

7. Apparatus according to claim 6 including a tube for collecting an oocyte connected with said aspiration tube, and wherein said second insulating jacket extends along a part at least of the length of said collecting tube.

8. Apparatus according to claim 5, including a source of flushing fluid and a connection by which said flushing fluid flows along said flushing tube.

9. Apparatus according to claim 8, wherein said source of flushing fluid includes a syringe connected with said tube and containing said flushing liquid, and wherein said first insulating jacket extends along at least a part of the length of said syringe.

10. Apparatus for use in extracting an oocyte comprising: an oocyte recovery needle; a flexible tube connected with said needle; a reservoir for receiving the oocyte; a connection between the reservoir and the flexible tube; a source of suction; a connection between the source of suction and the reservoir so that suction can be applied to draw an oocyte into the reservoir; a warming jacket surrounding said flexible tube; and a supply of warmed liquid connected with said jacket to warm said jacket and thereby warm said flexible tube so as to maintain the temperature of an oocyte flowing along said tube.

11. Apparatus according to claim 10, wherein said jacket is extruded.

* * * * *